(12) United States Patent
Schwartz et al.

(10) Patent No.: US 10,337,916 B1
(45) Date of Patent: Jul. 2, 2019

(54) METHOD TO OBTAIN FULL RANGE INTRINSIC SPECTRAL SIGNATURES FOR SPECTROSCOPY AND SPECTRAL IMAGING

(71) Applicant: Center for Quantitative Cytometry, San Juanj, PR (US)

(72) Inventors: Abraham Schwartz, San Juan, PR (US); Adolfas K. Gaigalas, Riviera Beach, FL (US); Peter Ingram, Raleigh, NC (US)

(73) Assignee: Center for Quantitative Cytometry, San Juan, PR (US)

( * ) Notice: Subject to any disclaimer, the term of this patent is extended or adjusted under 35 U.S.C. 154(b) by 0 days.

(21) Appl. No.: 15/949,929

(22) Filed: Apr. 10, 2018

(51) Int. Cl.
| | |
|---|---|
| *G01J 3/00* | (2006.01) |
| *G01J 3/02* | (2006.01) |
| *G01J 3/28* | (2006.01) |
| *G01J 3/42* | (2006.01) |
| *G01J 3/443* | (2006.01) |

(52) U.S. Cl.
CPC .......... *G01J 3/0297* (2013.01); *G01J 3/2823* (2013.01); *G01J 3/42* (2013.01); *G01J 3/443* (2013.01); *G01J 2003/2826* (2013.01)

(58) Field of Classification Search
CPC .......... G01J 3/0297; G01J 3/2823; G01J 3/42; G01J 3/443; G01J 2003/2826; G01N 21/274
USPC ................................................. 356/300, 307
See application file for complete search history.

(56) References Cited

U.S. PATENT DOCUMENTS

| | | | |
|---|---|---|---|
| 5,424,826 A * | 6/1995 | Kinney | G01J 3/2803 356/326 |
| 6,246,479 B1 * | 6/2001 | Jung | G01J 3/02 250/226 |
| 9,435,687 B1 | 9/2016 | Schwartz et al. | |
| 2016/0347482 A1 * | 12/2016 | Dimpfl | B64G 3/00 |
| 2018/0020129 A1 | 1/2018 | Schwartz et al. | |

* cited by examiner

*Primary Examiner* — Kara E. Geisel
*Assistant Examiner* — Jonathon Cook
(74) *Attorney, Agent, or Firm* — Hoglund & Pamias, PSC; Roberto J. Rios

(57) ABSTRACT

A method is provided to obtain a full range intrinsic spectral signature for spectroscopy and spectral imaging. The method eliminates the irrelevant spectral components and is used to normalize the spectral intensities across the full wavelength ranges obtained from different instrumentation. The method determines the intrinsic instrument noise levels and the noise level across the spectral range is averaged for each spectrum. By determining the percent of the integrated instrument noise relative to the integrated illumination energy for each instrument, the instrument noise can be normalized to one common value and the intensity values of the intrinsic sample spectra can be normalized proportionately and combined into a continuous intrinsic spectrum across the wavelength ranges of the contributing instruments. The methodology is also implemented in spectral imaging and spectral data cubes.

10 Claims, 12 Drawing Sheets

METHOD TO OBTAIN FULL RANGE INTRINSIC SPECTRAL SIGNATURES FOR SPECTROSCOPY AND SPECTRAL IMAGING

BACKGROUND OF THE INVENTION

Spectroscopy and spectral imaging have significantly progressed over the last hundred years employing the electromagnetic spectrum. However, spectroscopy has been developed for specific energy ranges, for example, x-ray dispersion, ultraviolet, visible, infrared, and microwave spectroscopies. These spectroscopic methods have adopted different units to describe the spectra derived within their specific energy range. For example, KeV is used for x-ray units, nm for ultraviolet and visible, wavenumber for infrared, and G-Hertz for microwave. Since these differing nomenclatures are different ways to refer to the electromagnetic spectrum, they can all be converted to a meter scale ranging from $10^{-1}$ to $10^8$ nm (nanometers). With this common unit, it is easy to understand the spectroscopic relationships across the electromagnetic energy range as shown in FIG. 1.

Spectral imaging, represented by multi-spectral and hyper-spectral imaging, is the formation of images constructed from spatial data describing a field of view and spectral data that provides correlated information to the positions of the materials in the field of view. With the advent of multi-spectral and hyper-spectral imaging, the concept of a spectral signature or fingerprint has been used since the spectra obtained from these imaging techniques is associated with a spectral description and definition a particular material. These terms are appropriate due to the complexity of the resulting spectra from a material of interest comprised of a multiple different molecules and compounds. Moreover, the clarity of hyper-spectral images and positive identification of the presence of specific elements, molecules and compounds is impeded by irrelevant spectral components, e.g., the illumination, background and instrument noise. All these spectral components significantly lower the signal to noise ratio. To better understand this phenomenon, FIG. 9 shows simulated spectra illustrating all the spectral components overlaid for ease of understanding. Illumination spectra of an illuminated sample material is illustrated by the area under the curve (A). Once the sample material is illuminated with the corresponding illumination source it will absorb some of that illumination energy as represented by the negative area (C) and will also emit or reflect some of that illumination energy as illustrated by the area under the curve (D). However, as previously explained noise as represented by (B) will always be present as part of the spectral components of a signal.

In order to understand the importance and the novelty of the present invention, it is necessary to define the concepts of intrinsic and irrelevant. The word intrinsic means, "belonging to a thing by its very nature" and is synonymous with terms like inherent, basic, essential, fundamental, central, core, key, innate, and underlying. On the other hand, the word irrelevant is associated with being immaterial, unrelated, extraneous, and unconnected. The basis of intrinsic spectroscopy and intrinsic spectral imaging according to the present invention, is built on these concepts and how they are applied to spectroscopy for producing consistent spectral signatures (fingerprints) independent of factors not associated with the material of interest, whether it is a single elemental, a molecular material, or a highly complex mixture of compounds. Therefore, Intrinsic Spectral Components are spectral component that arise from absorption of the illumination energy and Irrelevant Spectral Components are spectral components of the illumination energy that are not absorbed.

The basic principle of intrinsic spectroscopy is that intrinsic spectral components of a material of interest can only be generated when the material of interest absorbs energy. Once energy absorption occurs then that energy can interact with the material in different ways depending on the wavelength of the absorbed energy and the atomic content and molecular structure of the material of interest through atomic energy transitions and molecular bonding response, respectively. Any energy impinging on the material of interest that is not absorbed does not contribute to the material's intrinsic spectrum and is considered irrelevant.

The full range spectral signature or fingerprint of a material of interest would contain only the spectral components of the material of interest without irrelevant components from the illumination and background associated with spectrometer devices and sample chambers; this can be considered an intrinsic signature or fingerprint that is an assembly of intrinsic spectra across the full wavelength range.

Illumination Component

In general, an electromagnetic spectrum is generated when an atom, molecule, compound or material is illuminated by electromagnetic energy and absorbs specific ranges of the illumination energy, i.e., the absorption envelopes. The type of spectrum generated depends on how the sample (atom, molecule, compound or material) responds to the absorbed energy. It may allow the energy through (transmission spectroscopy), retain the energy (absorption spectroscopy), raise electrons to higher orbitals before dropping back to lower orbitals (fluorescence spectroscopy), or shift the illumination to a fixed wavelength distance (Raman Spectroscopy). In all cases, the absorption envelopes have a specific wavelength range with specific extinction coefficients for each wavelength within the absorption envelope. This describes the spectral profile/shape of the envelope. In classical spectroscopy, filters or lasers of narrow wavelengths are used that fall close to the maximum absorption of the envelope to illuminate sample of interest. However, when illuminating the sample with a wide range of wavelengths, only wavelengths that fall within the envelope are absorbed and can give rise to spectral components of the atom, molecule, compound or material in the sample. The tradeoff between these illumination conditions is resolution verses signal strength, respectively. All illumination wavelengths that are not absorbed can be considered as irrelevant spectral components of the illumination.

Background Component

Spectral components that are derived from background materials, e.g., the surface on which the sample resides or in the solution the sample is dissolved or suspended, may or may not be considered irrelevant in the analysis. This is determined on whether or not the background is important to the analysis and if the background is not included in the reference chamber. For a specific preparation of the sample, the irrelevant illumination and background spectral components are consistent and reproducible with respect to the resulting spectrum.

Environment Component

Environmental factors need to be considered as they affect the spectral response of a material of interest. These are variable conditions that affect the response of the material of interest, e.g., pH or the hydrophobicity of the support medium.

Instrument Noise

The spectral components arising from the instrument are considered random noise and vary each time a spectrum is obtained from the same specific sample, illustrated in FIG. 5 and FIG. 7. Random noise spectral components derive from electronic, mechanical and heat from the particular instrument. These spectral components will be present even when there are no sample or reference materials in the instrument. Since the instrument noise is random, and thus cannot be predicted, it cannot be absolutely removed from the intrinsic spectrum. Fortunately, the level of electronic noise in modern instrumentation is negligible, e.g., <2%, compared to the irrelevant illumination and background components. The method of removing the irrelevant spectral components of illumination has been described by the methodology explained in U.S. Pat. No. 9,435,687 to Schwartz et al, incorporated herein by reference in its entirety.

Spectral Wavelength Range

Another limitation of multi-spectra and hyper-spectra is the electromagnetic wavelength range available from the individual instrument's illumination energy that limit the spectral information available from the instrument. Consider the analogy of a person's name, e.g., John Smith. This information is not sufficient to identify a specific person within the population of the United States. However, if the name was Prof. Dr. John Benjamin Smith, III, this name most likely provides enough information to positively identify the person within the said population. In a similar manner, just having the visible spectrum of a compound indicating that it is red, is not sufficient to identify a molecule, such as, phycoerythrin. The present state of the art of hyper-spectral imaging can only make inference to the presence of phycoerythrin in a hyper-spectral image from the indication of a red spectral component occurring where phycoerythrin fluoresces and prior knowledge of the content of the sample, e.g., red-tide algae were known to be present in the imaging area. Positive identification requires that both infrared and fluorescence spectra show consistent chemical bonding and the wavelength positions and separations of the absorption (inverted excitation) and emission peaks, i.e., the Stoke's shift. The spectral signature and absorption envelope for this example could range from the near ultra violet (400 nm) to the far infrared (2000 nm).

A complete intrinsic spectral signature of a molecule or compound would theoretically encompass the whole electromagnetic range from wavelengths from zero to infinity. However, an achievable practical extended wavelength spectrum may range from 0.1 Angstrom (a electron beam) to 100 centimeter (microwaves). Such a spectrum would contain intrinsic spectral components from elements obtained from x-ray spectroscopy, transition state spectral components from UV, visible and infrared spectroscopy and size and rotational spectral components from microwave spectroscopy. By simply combining spectra from classical spectrometry does not provide an acceptable continuous spectrum when filters and laser lines are used for illumination. The combined spectra would have gaps caused by the absorption gaps in the wavelength range due to incomplete illumination across the absorption wavelength range and the lack of intensity normalization across the different instrumentation.

Thus, what is needed is a system and a method for obtaining a full range intrinsic spectral signature for spectroscopy and spectral imaging without the limitations of the current technologies.

SUMMARY OF THE INVENTION

The present invention provides a system and a method for obtaining a full range intrinsic spectral signature for spectroscopy and spectral imaging without the need of post-acquisition modeling to remove irrelevant spectral components.

According to an aspect of the invention, the system and methodology eliminates the need for filters to isolate specific illumination wavelengths.

According to another aspect of the invention, a consistent intrinsic signature/fingerprint of the material of interest is always achieved.

According to still another aspect of the invention, measurements of instrument noise can be isolated from all other spectral components.

According to one aspect of the invention, increased signal intensity can be obtained due to absorption over the whole absorption envelop.

According to another aspect of the invention, spectral components that were masked by the irrelevant illumination are now revealed and identifiable.

According to a further aspect of the invention, each spectroscopic instrument is balanced, and an average percent intrinsic instrument noise is determined for the spectroscopic instrument.

According to still another aspect of the invention, the average percent instrument noise of each instrument is normalized to the instrument with the lowest average percent instrument noise level to obtain a normalized noise factor for each instrument.

According to one aspect of the invention, an intrinsic spectrum profile of a sample material is obtained from each balanced spectroscopic instrument covering a different wavelength range.

According to another aspect of the invention, a normalized intrinsic spectrum of the sample material is obtained for each instrument by proportionally adjusting the intensity levels of the intrinsic spectrum profile across the instrument wavelength range by the normalized noise factor.

According to yet another aspect of the invention, a wavelength axis of each normalized intrinsic spectrum of the sample material is converted into a log scale.

According to still another aspect of the invention, a full range intrinsic spectrum of the sample material is constructed by arranging the normalized intrinsic spectrum of the sample material of each instrument on the electromagnetic continuum in relationship to each other so that the arrangement represents the wavelength range covered by all the plurality of balanced spectroscopic instruments.

According to one aspect of the invention, if there are overlapping regions on respective ends of neighboring spectra from adjacent balanced spectroscopic instruments once the full range intrinsic spectrum is constructed, an entire normalized intrinsic spectral intensity profile from one of the adjacent balanced spectroscopic instrument is adjusted proportionally so that the intensities of the spectra on the overlapping regions are equal at the same wavelengths.

According to another aspect of the invention, the normalized intrinsic spectrum is obtained by normalizing an integrated intrinsic absorption profile and an integrated intrinsic emission profile of the sample material.

According to yet another aspect of the invention, the method is used with spectral cameras covering different wavelength ranges associated to data on a pixel of a spatial field of view of a spectral data cube.

According to an aspect of the invention, each pixel of a data cube contains intrinsic spectral data of the spatial field of view for a wavelength range covered by all the spectral cameras.

According to another aspect of the invention, the full range intrinsic spectra of the sample material is obtained from the data cube comprising a plurality of pixels containing data of the spatial field of view.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The present invention provides a method to obtain a full range intrinsic spectral signature for spectroscopy and spectral imaging. This method eliminates the irrelevant spectral components and proposes a novel methodology to normalize the spectral intensities across the full wavelength ranges obtained from different instrumentation. This methodology takes advantage that the ratio of the intrinsic noise level to the intrinsic sample intensities are proportional and independent of the gain settings and duration of data collection.

The methodology of the present invention determines the intrinsic instrument noise levels as described in U.S. Pat. No. 9,435,687, incorporated herein by reference in its entirety. As shown in plots a-c of FIG. 7, the spectral components of the instrument noise vary in wavelength position and intensity due to the fact that noise is random. However, the noise level across the indicated spectral range can be averaged for each spectrum. It is expected that the average value of noise is comparable. However, this would not necessarily be the case when comparing the average noise levels from different instruments set to analyze a different wavelength range. By determining the percent of the integrated instrument noise relative to the integrated illumination energy for each instrument, the instrument noise can be normalized to one common value and the intensity values of the intrinsic sample spectra can be normalized proportionately and combined into a continuous intrinsic spectrum across the wavelength ranges of the contributing instruments. The intensities of the intrinsic spectral components derived from instruments can be further refined where the wavelength ranges of the instruments overlap.

Figure 3:
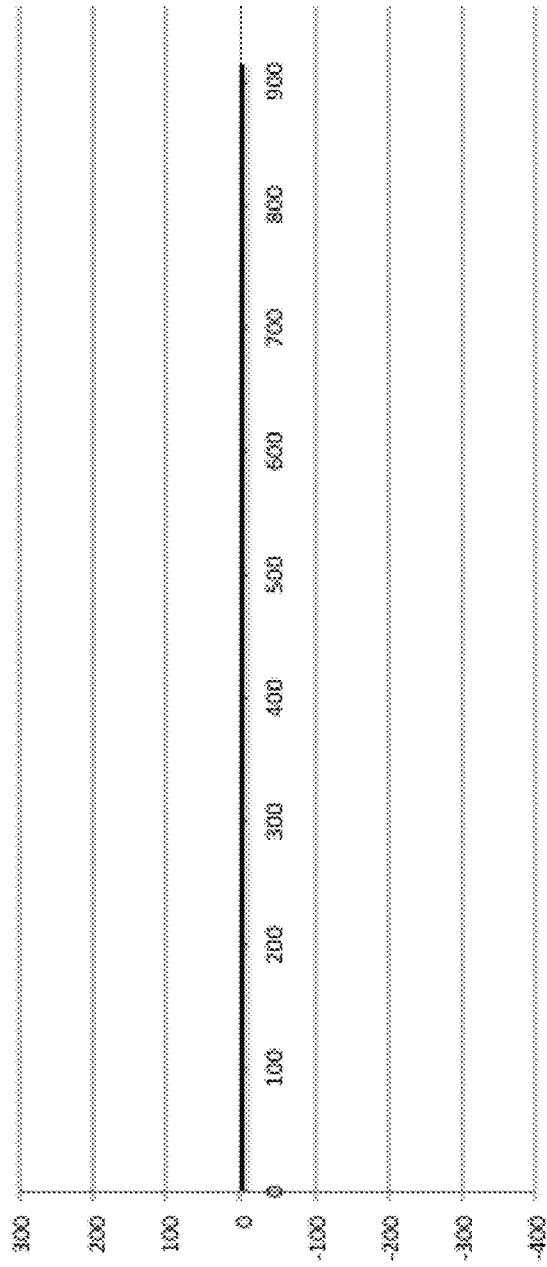
FIG. 3 shows the zero-order spectrum representing the spectrum of a balanced instrument after adding the residual spectrum to the reference spectrum and subtracting the sum from the sample spectrum from an unbalanced instrument.
Figure 4:
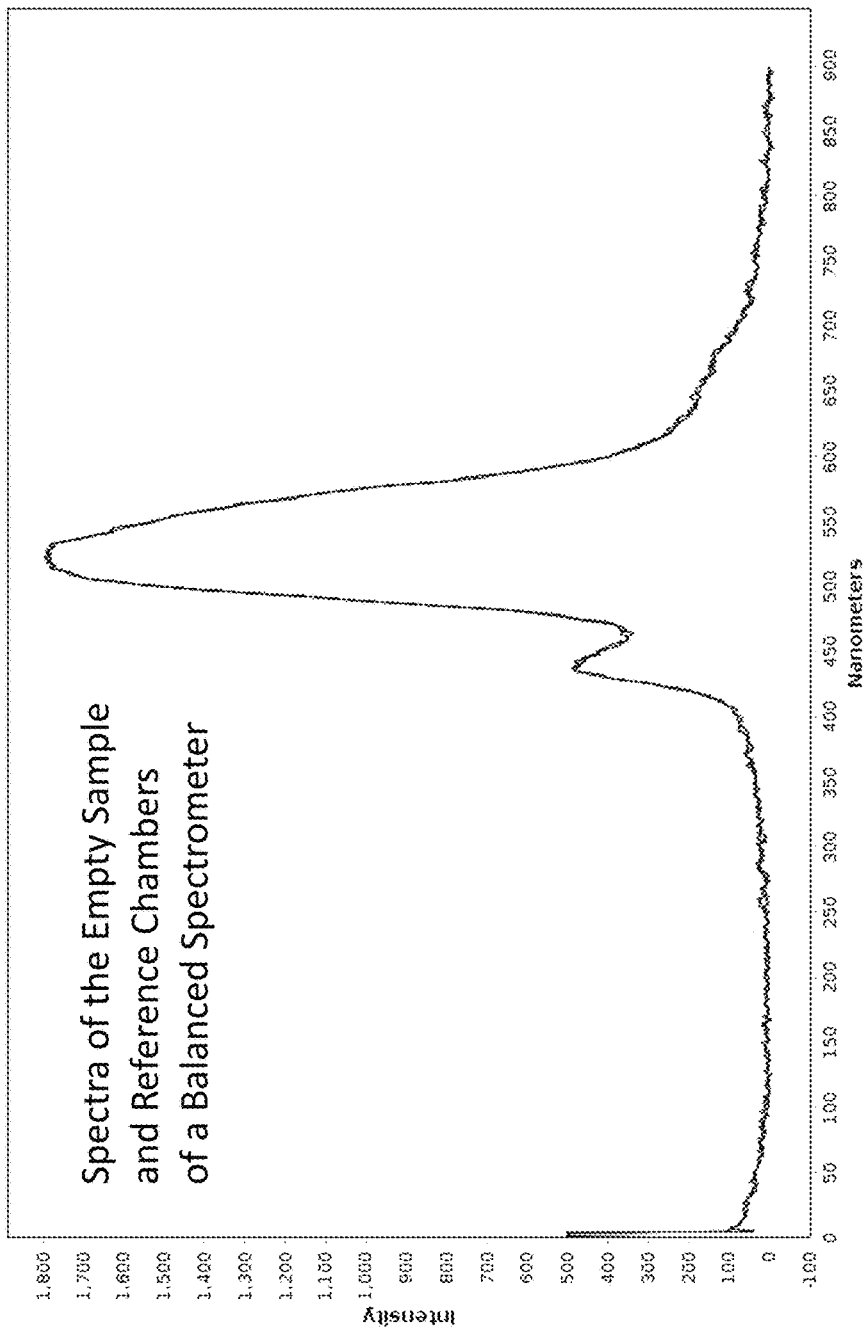
FIG. 4 shows the superimposed first order spectra of a new set of data from the empty reference and sample chambers after the instrument is balanced.
Figure 5:
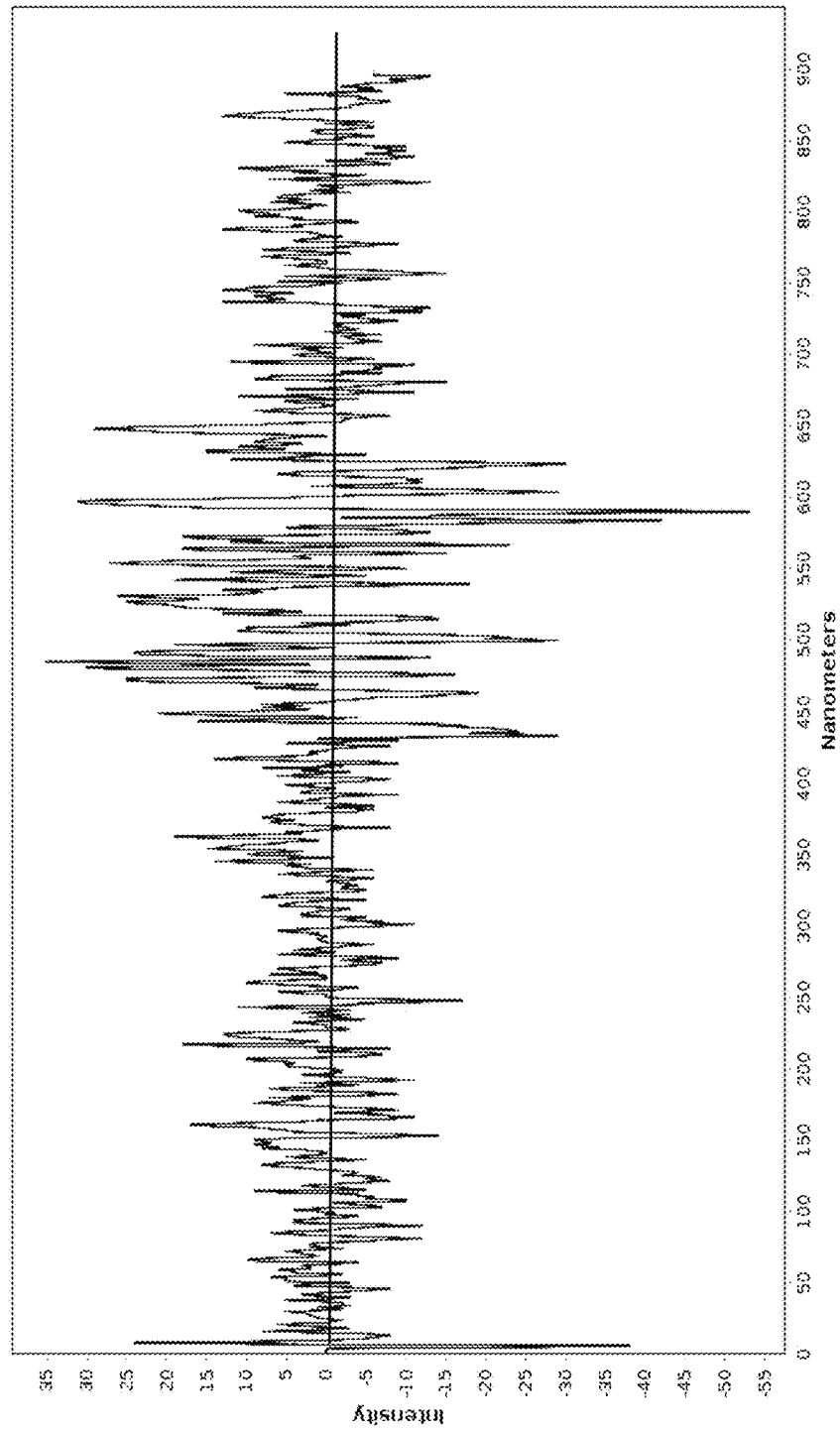
FIG. 5 shows the intrinsic spectrum of the instrument noise obtaining from the new set of data from the empty reference and sample chambers by subtracting the residual spectrum added to the new reference spectrum from the new sample spectrum after the instrument is balanced.
Figure 6:
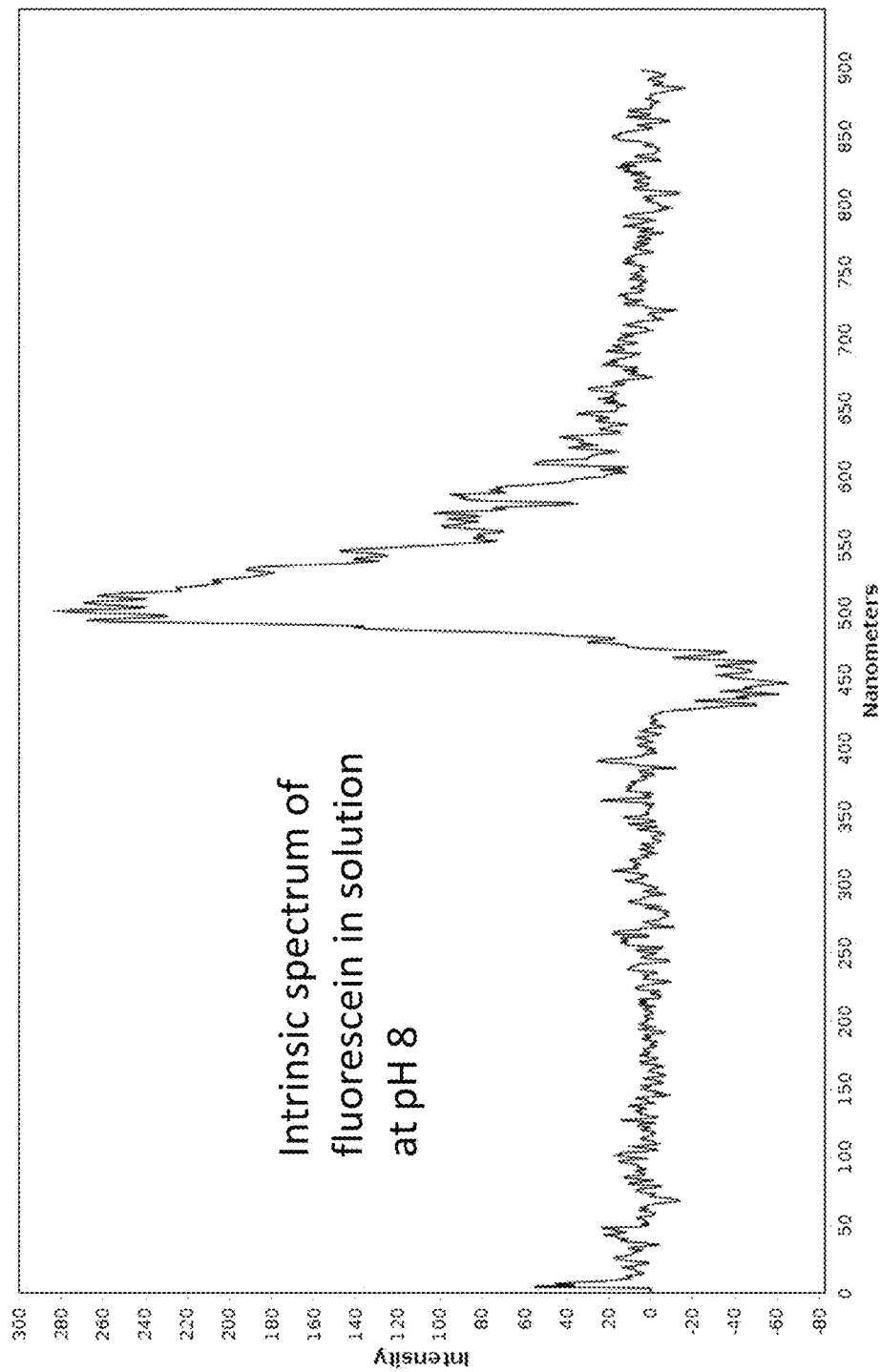
FIG. 6 shows the intrinsic spectrum of a fluorescein solution at pH 8 from a balanced instrument.

According to the invention, intrinsic spectral data is obtained from illumination wavelength from electrons to microwaves (0.1 A-10 cm) according to the methodology described in U.S. Pat. No. 9,435,687, incorporated herein by reference in its entirety. This would require data from an electron dispersive spectrometer, x-ray spectrometer ultraviolet spectrometer, visible spectrometer, infrared spectrometer, and microwave spectrometer. According to the methodology, reference and sample spectra obtained from empty chambers are balanced such that the intensity across the total wavelength range of the illumination is zero. This spectrum contains no spectral components from the sample, reference, background, illumination or noise. This spectrum is referred to as the Zero Order Spectrum. Under this instrument setup, subsequent spectra obtained from a material of interest will yield its intrinsic spectral components. The Zero Order Spectrum is obtained in the following manner. An initial reference and a sample spectrum are obtained across the total wavelength range of the single instrument that are empty of any sample or reference material. These spectra are obtained at exactly the same time and under the same environment conditions, i.e., illumination wavelength range and intensity, atmosphere, sample holder, instrument response, etc. Note that no optical filters are used in this process. The empty reference spectrum is subtracted, wavelength by wavelength, from the empty sample spectrum yielding a Residual Spectrum which is added back, wavelength by wavelength, to the original empty reference spectrum. Finally, this resulting spectrum is then subtracted, wavelength by wavelength, from the original sample spectrum yielding the Zero Order Spectrum where all values along the wavelength range of the instrument are zero, as can appreciated from FIG. 3. Note that the residual spectrum contains the noise component from the initial set of spectra.

The importance of the Zero Order Spectrum is that all irrelevant spectral components have been eliminated, including the illumination spectrum and the noise. This result follows from the above definition of Intrinsic Spectral Components where spectral component only arises from absorption of the illumination energy. Since there is no reference and sample material in the instrument to absorb energy, there can be no intrinsic spectral components in the Zero Order Spectrum. When the residual spectrum is added to the reference spectrum of subsequent empty reference-sample spectral data sets, the resulting spectrum is the isolated noise spectrum of the instrument. Since noise is random each of the subsequent data sets will produce spectra containing different noise spectral components. Only the isolated instrument noise spectrum is present since the total illumination energy is still considered irrelevant because none of the illumination energy is absorbed without any reference and sample materials. Unfortunately, in practice, this means that random spectral noise components of the instrument will be a component of intrinsic spectra. However, by taking spectra empty reference and sample materials, the spectral noise level can be isolated, identified and quantified with respect to the intrinsic spectrum.

Once each of the instruments have been balanced by the above-explained method, the present inventive methodology is performed to produce a full range intrinsic spectrum for a sample material.

Determine the Average Intrinsic Noise for Each Individual Instrument.

Figure 7:
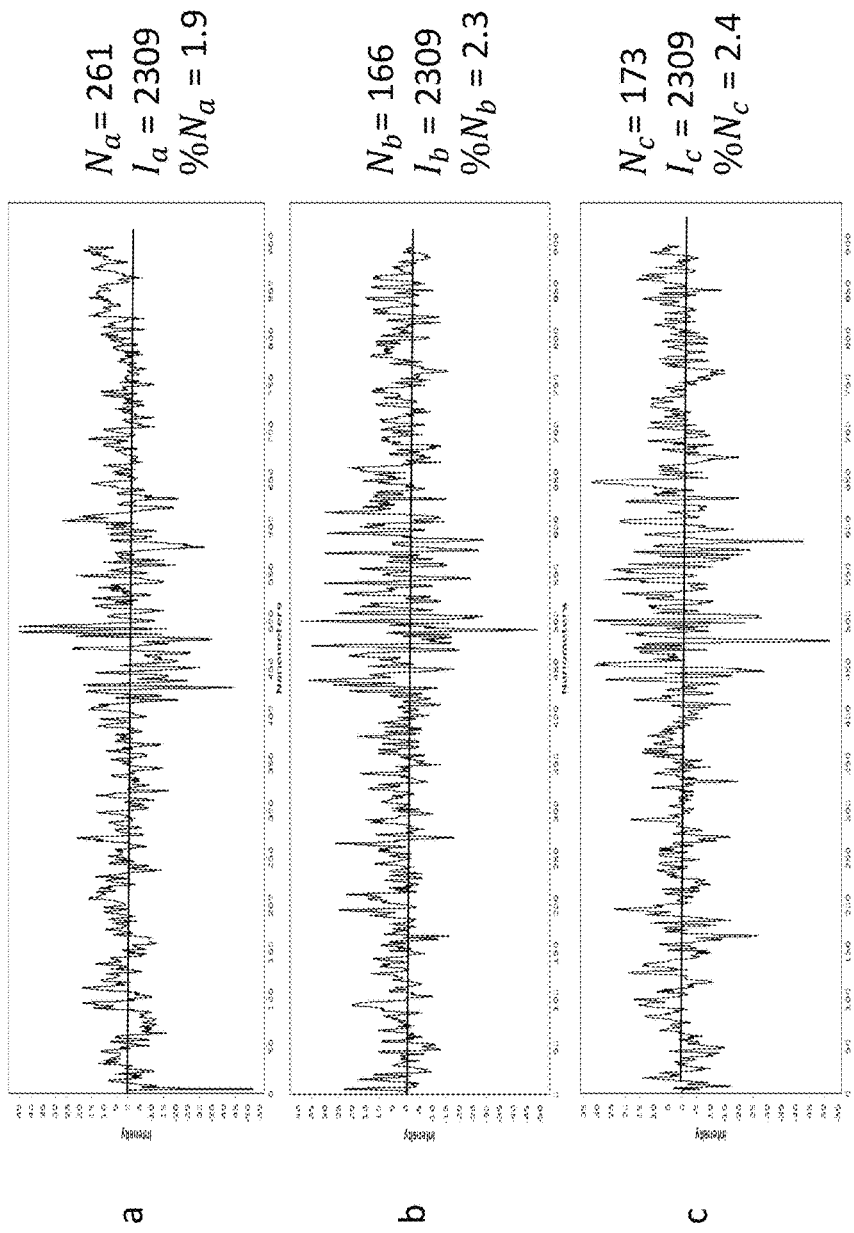
FIG. 7 shows three different intrinsic noise spectra repetitively obtained from a balanced instrument demonstrating that instrument noise is a random event.
Figure 9:
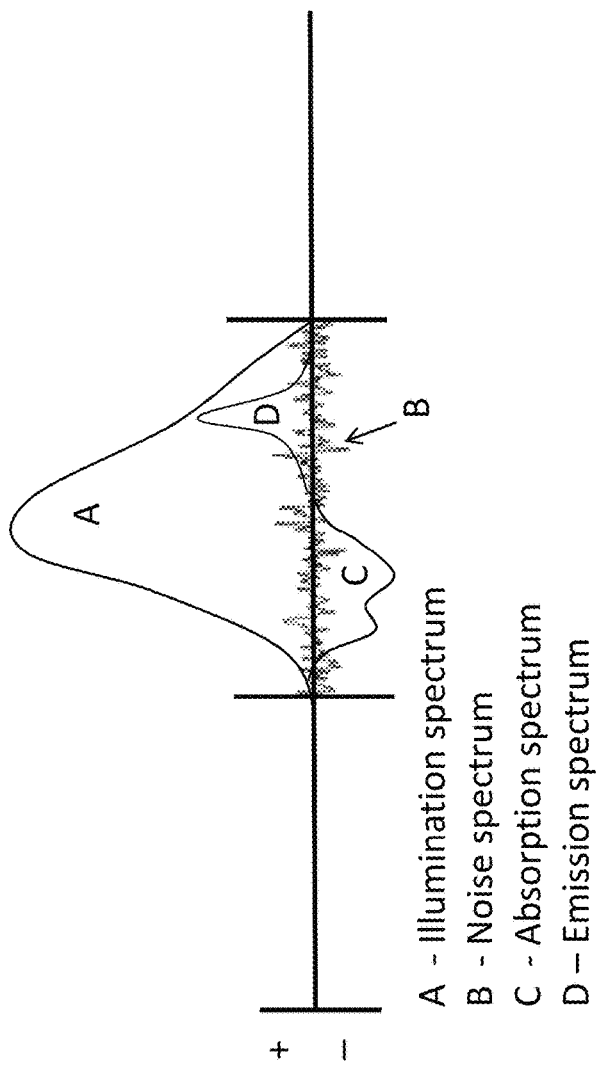
FIG. 9 shows an example of spectral signal illustrating all its components.
Figure 10:
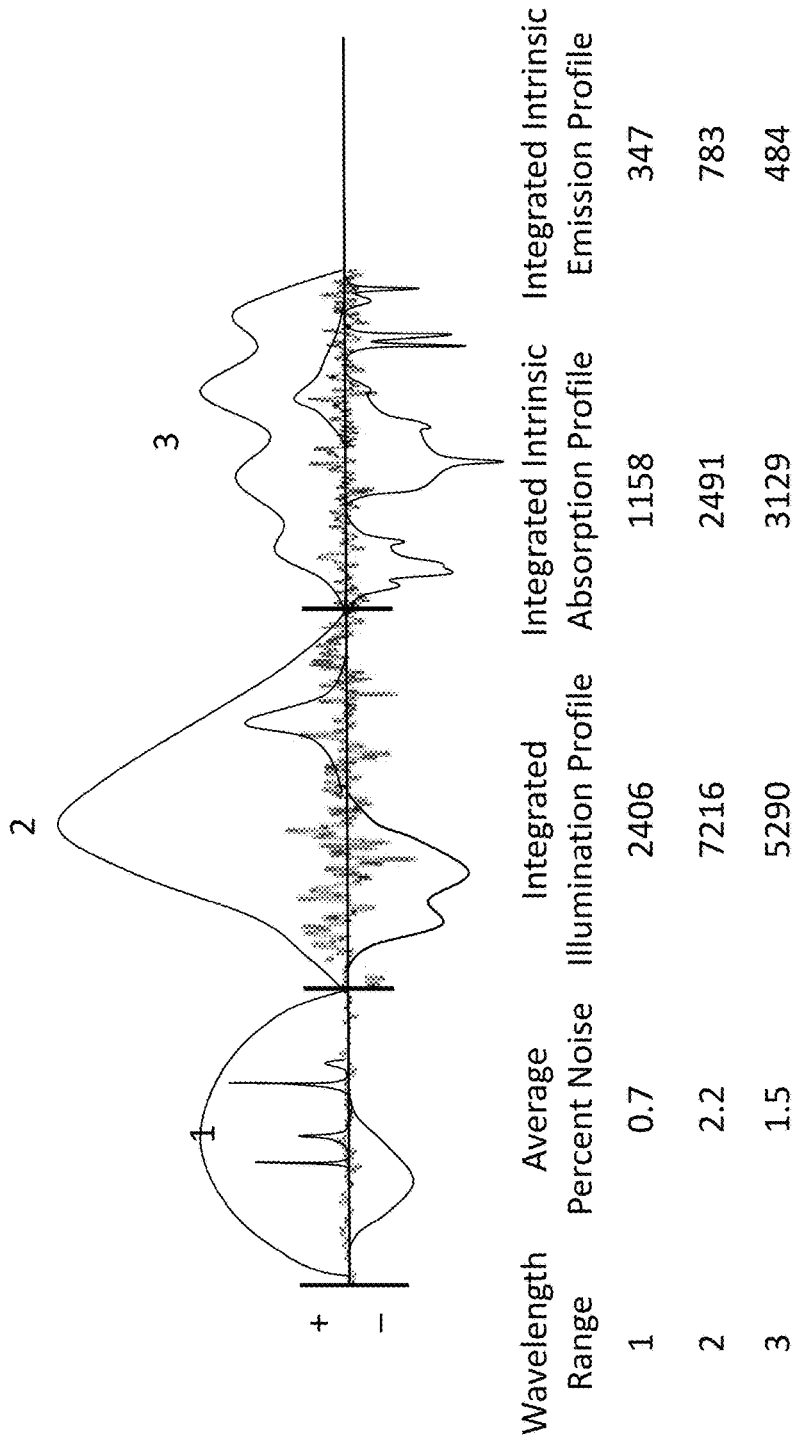
FIG. 10 shows an example of combined un-normalized spectra, according to the present invention.

With the reference and sample chambers empty, a plurality of intrinsic spectra of the balanced instrument is obtained representing the instrument noise. Note that these multiple noise spectra are different in peak positions and intensities, confirming that the noise is random, FIG. 7. Then, the percentage of intrinsic noise intensity relative to an illumination intensity of said spectroscopic instrument is determined for each of said plurality of intrinsic spectra of the balanced instrument. This is given by the following expression: $N_a/I_a$, where $N_a$ is the total intensity of the intrinsic noise spectra (a) of the balanced instrument and $I_a$ is the total intensity of the illumination spectra of the balanced instrument. This is better understood in conjunction with the spectrum illustrated in FIG. 9 where: 1) only the area inside the negative region of the entire wavelength range of the noise spectra (B) is calculated since anything that is not absorbed (i.e., shown on the positive Y axis) does not contribute to the intrinsic spectrum and is considered irrelevant, 2) the area inside the illumination spectra (A) is calculated, and 3) the calculated area of the noise spectra is divided by the calculated area of the illumination spectra to obtain the percentage intrinsic noise intensity of the instrument. According to the example for an instrument (2) as shown in FIGS. 7, 9 and 10, this would be calculated:

$$\% \ N(2)_a = N_a/I_a = 261/2309 \times 100 = 1.9\%$$

$$\% \ N(2)_b = N_b/I_b = 166/2309 \times 100 = 2.3\%$$

$$\% \ N(2)_c = N_c/I_c = 173/2309 \times 100 = 2.4$$

Finally, an average percent intrinsic instrument noise for the spectroscopic instrument is determined by averaging the percentage intrinsic noise intensities of said plurality of instrument noise spectra. In the example instrument (2) this is calculated, $$\% \ N(2)_{ave} = \frac{\% \ N(2)_a + \% \ N(2)_b + \% \ N(2)_c}{3} = \frac{1.9 + 2.3 + 2.4}{3} = 2.2$$

Normalize the Intrinsic Spectral Intensities Across Instruments.

A sample material for analysis by each of the participating instruments is prepared in the appropriate formats. Then, a normalized noise factor $NF_{form}$ is calculated for each instrument by normalizing the average percent intrinsic instrument noise of each instrument to the instrument with the lowest average percent intrinsic instrument noise level. In the example illustrated in FIGS. 10 and 11, this will be calculated:

$$NF(1)_{norm} = \frac{\% \ N_{lowest}}{\% \ N(1)_{ave}} = \frac{0.7}{0.7} = 1$$

$$NF(2)_{norm} = \frac{\% \ N_{lowest}}{\% \ N(2)_{ave}} = \frac{0.7}{2.2} = 0.32$$

$$NF(3)_{norm} = \frac{\% \ N_{lowest}}{\% \ N(3)_{ave}} = \frac{0.7}{1.5} = 0.47$$

Figure 11:
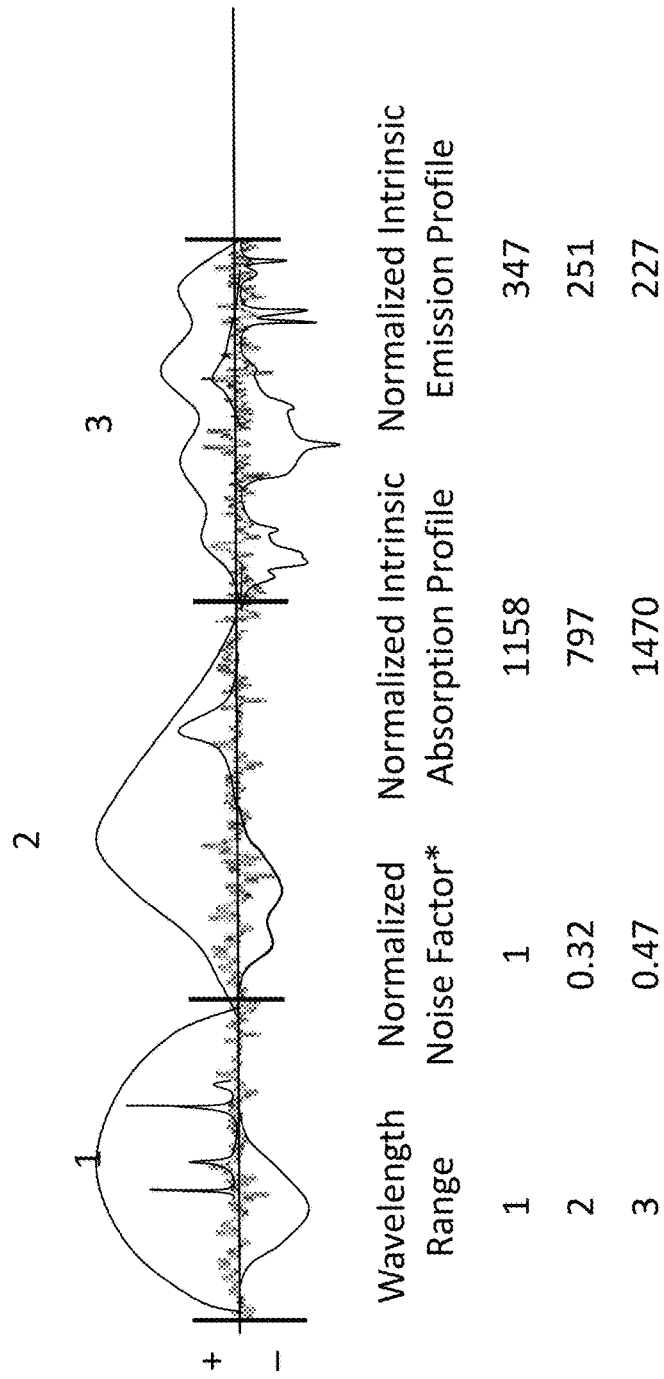
FIG. 11 shows an example of combined normalized spectra, according to the present invention.

Then, the previously prepared sample materials are illuminated to obtain an intrinsic spectrum profile (Integrated Absorption Profile, Integrated Emission Profile) of a sample material from each balanced spectroscopic instrument covering a different wavelength range, as illustrated in FIG. 10. Afterwards, a normalized intrinsic spectrum of the sample material is obtained for each instrument by proportionally adjusting the intensity levels of the intrinsic spectrum profile across the instrument wavelength range by said normalized noise factor, as illustrated in FIG. 11. For the example instrument (2), this is calculated by multiplying its Integrated Intrinsic Absorption Profile $IIAP_2$ and its Integrated Intrinsic Emission Profile $IIEP_2$ by its normalized Noise Factor $NF(2)_{norm}$.

$$IIAP_2 \times NF(2)_{norm} = 2491 \times 0.32 = 797$$

$$IIEP_2 \times NF(2)_{norm} = 783 \times 0.32 = 251$$

Construction of the Full Range Intrinsic Spectrum.

Figure 1:
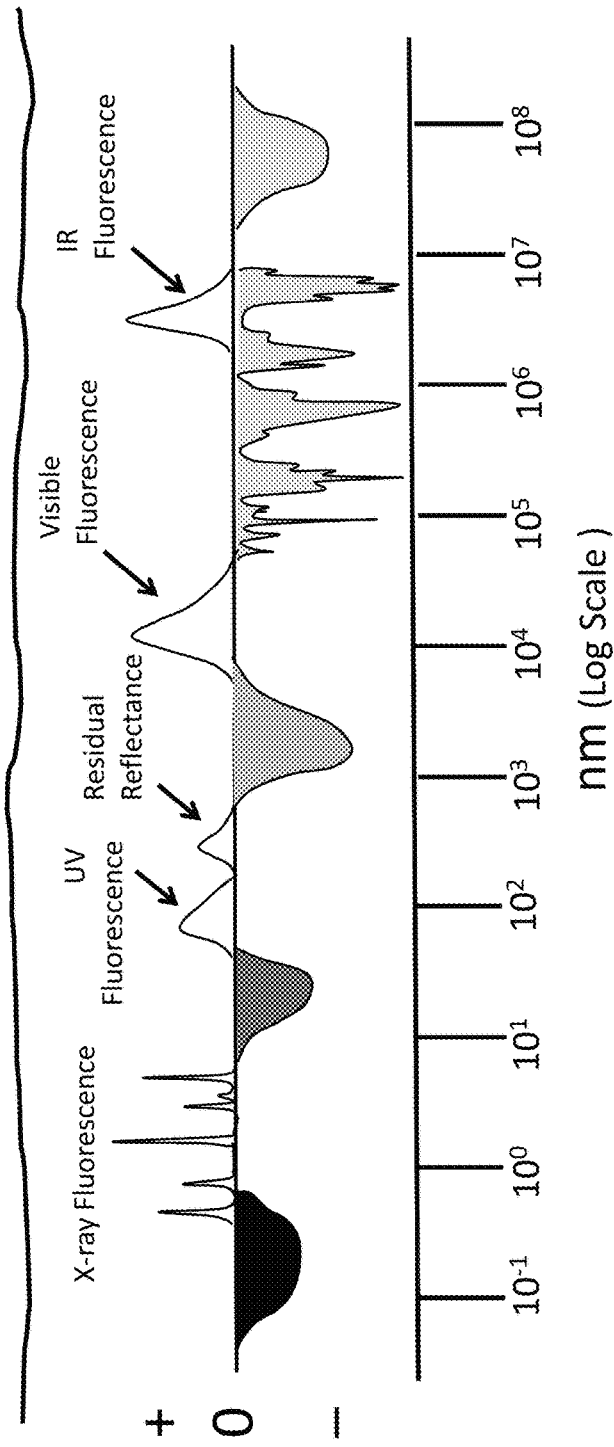
FIG. 1 illustrates an intrinsic spectrum covering a wavelength range $10^{-1}$ nm to $10^8$ nm indicating the specific wavelength range covered by the different spectroscopic instruments.
Figure 2:
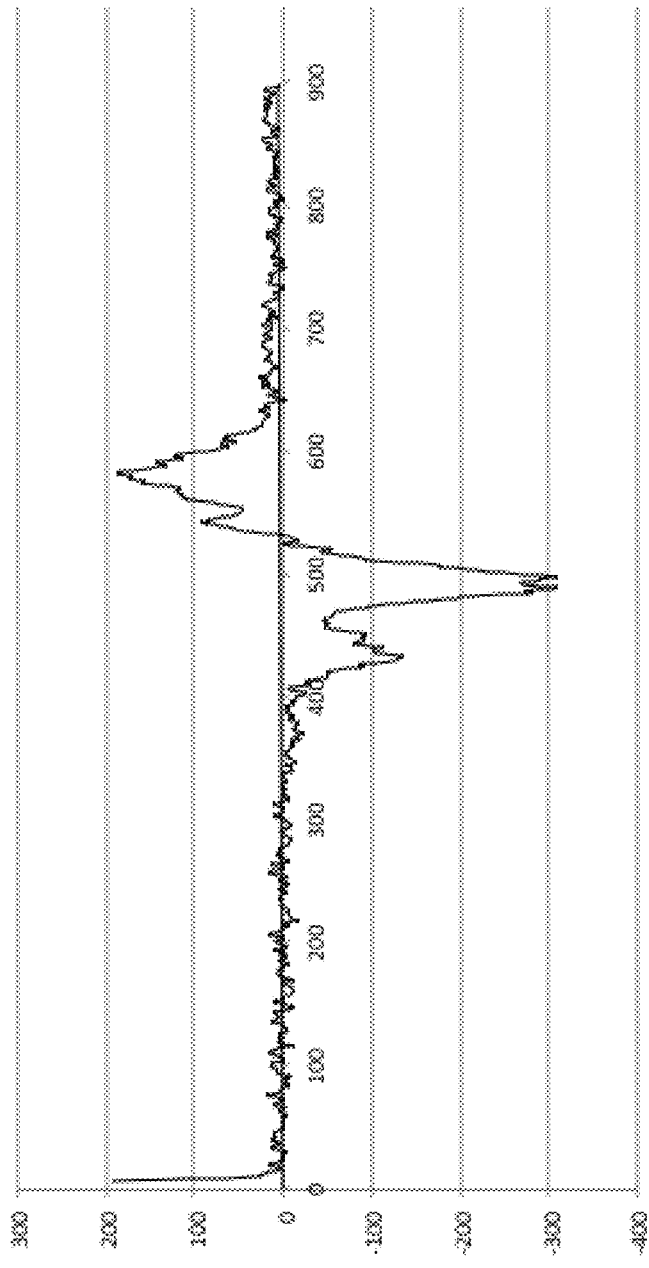
FIG. 2 shows the residual spectrum representing the difference between the spectra from an empty reference chamber and an empty sample chamber from an unbalanced instrument.
Figure 8:
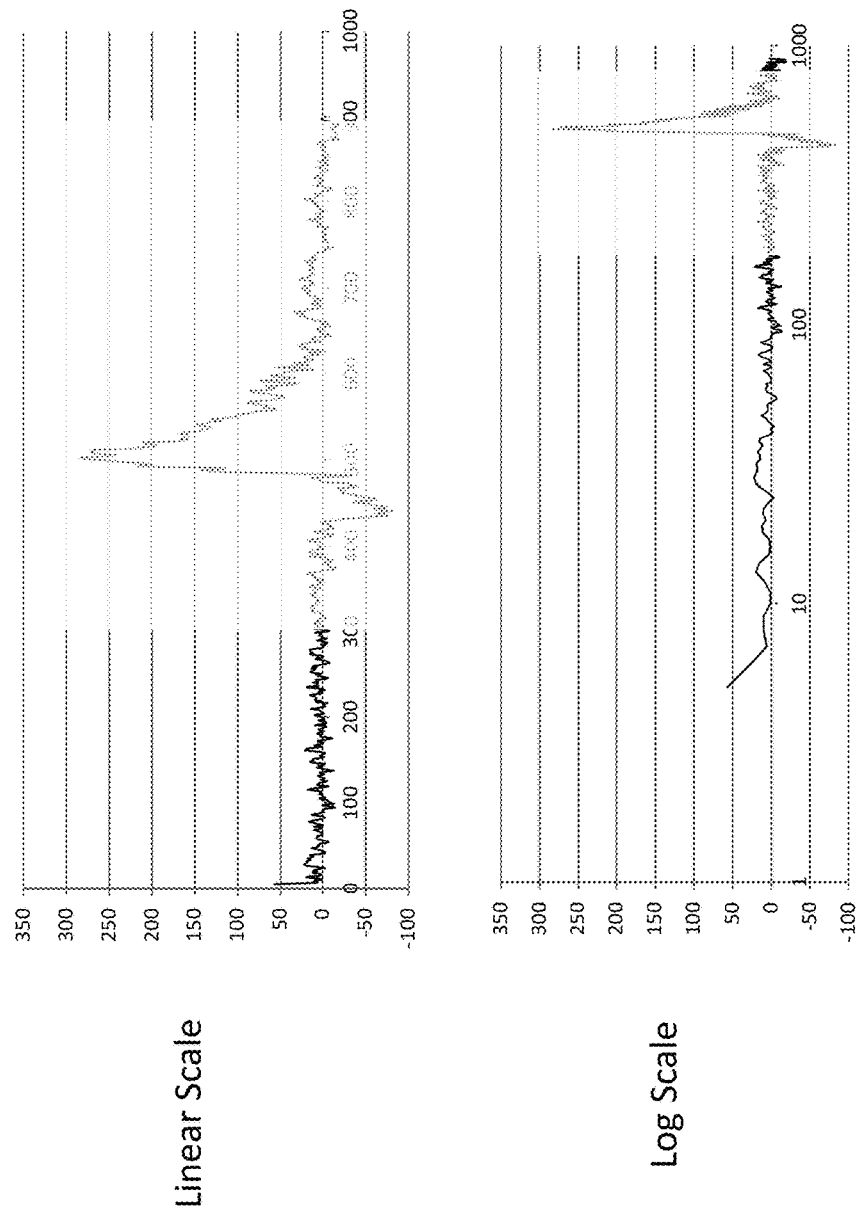
FIG. 8 shows the conversion of a linear intrinsic spectrum to a log intrinsic spectrum.

When attempting to display a full intrinsic spectrum, a linear depiction is not practical since it could have a range over nine decades, e.g., 1-1,000,000,000, as indicated in FIG. 1. However, if the intrinsic spectral range is converted to a log scale, the full range of data can be presented as a single continuous spectrum. An example of such a conversion is presented in FIG. 8. In both the linear and log representations of the spectrum, a relevant wavelength range needs to be defined. Since the intrinsic spectrum arises from the absorption of the illumination energy, it follows that no relevant spectral components can have lower wavelengths than the lowest wavelength of the illumination. Therefore, the relevant wavelength range for a specific instrument can be defined from the lowest illumination wavelength to its highest detection wavelength, as shown by the grey linear and log areas in FIG. 8. The grey area ranges from the different instruments can then be combined into a full intrinsic spectrum/signature of a material.

Each of the wavelength axes of the normalized intrinsic spectra is converted into a log scale and arranged on the electromagnetic continuum in relationship to each other such that they describe the wavelength range covered by all the participating instruments, as shown in FIG. 11. Where there are overlaps on the respective ends of the neighboring spectra from different instruments, the entire intrinsic spectral intensity profile from that instrument is adjusted proportionally such that the intensities are equal at the same wavelengths.

A full range intrinsic spectrum of a material provides a complete set of information on how a particular compound responds to being illuminated by a wide range of electromagnetic energy while eliminating the irrelevant spectral components of illumination and background. The full range intrinsic spectrum is responsive to environmental factors since such factors can affect the chemical state and structure of the molecules thus changing how the illumination is absorbed and interacts with the compound. In addition, a full range intrinsic signature from a material that contains numerous different atoms, molecules and compounds provides a complete set of information on how a particular material responds to being illuminated by a wide range of electromagnetic energy while eliminating the irrelevant spectral components of illumination and background. Again, this signature is dependent on the environment that can affect the chemical state and structure of the material.

Construction of Full Spectrum Multi-Spectral and Hyper-Spectral Images

When the full range intrinsic spectral signature is applied to multi-spectral and hyper-spectral imaging, complete spatial/spectral information is obtained for the field of view with respect to the location of; elements, molecules, compounds and materials are present, therein. This is because each pixel of the spatial image is associated with its full intrinsic spectrum carrying the full intrinsic signature of the materials. Note that when constructing spectral images, it is not necessary to convert to a wavelength scale since most computers can accommodate a full intrinsic spectrum of nine orders of magnitude.

The present invention provides a method to obtain a full intrinsic spectrum of a material of interest by applying the methodology to obtain the intrinsic spectrum of such a material of interest over a relatively short wavelength range from a single instrument, as explained in U.S. Pat. No. 9,435,687 (incorporated herein by reference in its entirety). By taking the short range intrinsic spectra from a plurality of instruments covering different illumination ranges and using the proportional relationship between the noise and illumination levels and subsequently equalize the noise levels across instruments to, in turn, normalize the intrinsic spectral components obtained from those instruments, the full intrinsic spectrum of the material of interest can be obtained across the wavelength ranges of the combined instruments.

The present invention is also useful when developing libraries of full range intrinsic spectra of various materials of interest, where such intrinsic spectra would provide a more complete spectral signature of the materials than intrinsic spectra obtained from a single instrument with a shorter illumination wavelength range. Accordingly, the methodology to obtain wide intrinsic spectra is extremely useful and convenient when applied to spectral imaging where it is highly important to obtain definitive identification of materials in the field of view. This is because the wider the illumination wavelength range, the more likely the intrinsic spectra will contain more intrinsic spectral components from the materials in the field of view.

Figure 12:
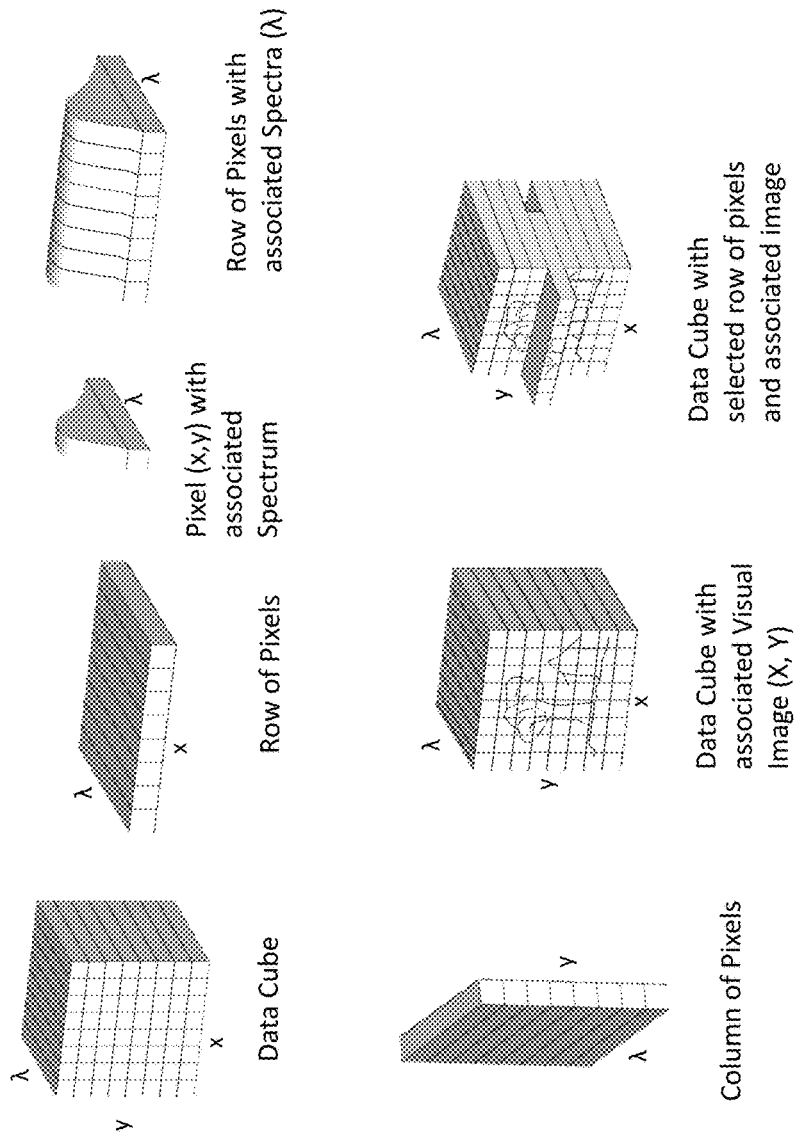
FIG. 12 shows the structure of a spectral data cube, according to the present invention.

The structure of a data cube is illustrated in FIG. 12. Two hyper-spectral or multi-spectral cameras or data sources are used to obtain a reference data cube and a sample data cube, respectively, of empty space at the same time and under the same environmental conditions such that the input spectral data in the empty reference data cube and the empty sample data cube are the same. The outputs of the cameras or sources are then balanced (as previously explained) so that all spectral intensity values of the resulting data cube, referred to as the Balanced Data Cube, are all zero. This indicates that there are no spectral illumination and background components present in the Balanced Data Cube. The associated spectrum of each pixel (x,y) can be acquired from a single spectral camera or a plurality of spectral cameras each one covering a different wavelength range. The method for removing the spectral components of illumination and background from multi-spectral and hyper-spectral images is explained in co-owned U.S published application 2018/0020129A1 which is incorporated herein in its entirety.

Accordingly, the methodology of the present invention is applied to spectral imaging by synchronizing two or more spectral cameras covering different illumination wavelength ranges toward the same field of view such that spatial and spectral data for the reference field and the sample field are taken simultaneously, and intrinsic spectra is obtained for each pixel of the spatial field of view. The first step to get the wide wavelength intrinsic spectra is to obtain reference and sample spectra from a field of view that has no reference or sample materials, e.g., empty sky or an empty microscope slide. Then, obtain the zero-order spectrum for each instrument by finding the residual spectrum and adding it to the reference spectrum from each of the instruments, then subtracting that sum from the sample spectrum. The average isolated noise level of each instrument is then obtained from a subsequent plurality of data sets of the empty field of view. The ratios of the average noise levels from the different instruments are determined by dividing the lowest noise level by each of the other instrument noise levels. The intensities of the intrinsic spectral components from each instrument are then multiplied by the respective noise ratio to normalize their intensities across the wavelength range of the instruments. These intrinsic spectral components can now be combined into a wide intrinsic spectrum. When this procedure is performed for the spectral data associated with each pixel of the field of view, the result is a data cube that has a wider range intrinsic spectrum associated with each respective pixel. These intrinsic spectra resulting from extended illumination wavelength range provides a more definitive signature for the materials in the field of view since they will consist of more intrinsic spectral components. Thus, according to an embodiment of the invention, full range intrinsic spectral signatures for a material of interest can be obtained from a spectral data cube by synchronizing and balancing (i.e., zero-order spectrum) spectral cameras covering different wavelength ranges and implementing the inventive methodology of the present invention to obtain full range intrinsic spectral signatures for a material of interest from intrinsic spectra contained on each pixel of the data cube. The above-explained methodologies are described in more detail in co-owned U.S. Pat. No. 9,435,687 and US published application 2018/0020129A1, both documents are incorporated herein by reference in its entirety.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A method of displaying a generated full range intrinsic spectrum of a sample material comprising:
   a) performing for each of a plurality of spectroscopic instruments, each spectroscopic instrument covering a different wavelength range, the steps of:
      I. balancing the spectroscopic instrument so that irrelevant spectral illumination and background components are eliminated from intrinsic spectra of each spectroscopic instrument,
      II. obtaining a plurality of instrument intrinsic noise spectra from said balanced spectroscopic instrument, III. determining for each said plurality of instrument intrinsic noise spectra a percentage intrinsic noise intensity relative to an illumination of said spectroscopic instrument, IV. determining an average percent intrinsic instrument noise for the spectroscopic instrument by averaging the percentage intrinsic noise intensity of said plurality of instrument noise spectra;

b) normalizing the average percent instrument noise of each instrument to the instrument with the lowest average percent instrument noise level to obtain a normalized noise factor for each instrument;

c) obtaining from each balanced spectroscopic instrument covering a different wavelength range, an intrinsic spectrum profile of a sample material;

d) obtaining for each instrument a normalized intrinsic spectrum of the sample material by proportionally adjusting the intensity levels of the intrinsic spectrum profile across the instrument wavelength range by said normalized noise factor;

e) converting a wavelength axis of each normalized intrinsic spectrum of the sample material into a log scale;

f) generating a full range intrinsic spectrum of the sample material by arranging the normalized intrinsic spectrum of the sample material of each instrument on the electromagnetic continuum in relationship to each other so that the arrangement represents the wavelength range covered by all the plurality of balanced spectroscopic instruments; and g) displaying said generated full range intrinsic spectrum of the sample material.

2. The method of claim 1, wherein if there are overlapping regions on respective ends of neighboring spectra from adjacent balanced spectroscopic instruments once the full range intrinsic spectrum is constructed, an entire normalized intrinsic spectral intensity profile from one of said adjacent balanced spectroscopic instrument is adjusted proportionally so that the intensities of the spectra on the overlapping regions are equal at the same wavelengths.

3. The method of claim 1, wherein the percentage intrinsic noise intensity for each of said plurality of instrument intrinsic noise spectra is determined by the following equation:

$$\% N_a = \frac{N_a}{I_a} \times 100$$

where $N_a$ is the total intensity of an intrinsic noise spectra (a) of a balanced instrument and $I_a$ is the total intensity of the illumination spectra of the balanced instrument.

4. The method of claim 3, wherein said total intensity of the intrinsic noise spectra $N_a$ is determined by calculating only the area inside the negative region of the entire wavelength range of the intrinsic noise spectra and said total intensity of the illumination spectra $I_a$ is determined by calculating the area inside the illumination spectra of the balanced instrument.

5. The method of claim 1, wherein the normalized noise factor for each instrument is determined by the following equation:

$$NF_{norm} = \frac{\% N_{lowest}}{\% N_{ave}},$$

wherein $\% N_{ave}$ is the average percent intrinsic noise of the instrument and $\% N_{lowest}$ is the lowest average percent intrinsic noise level among all instruments.

6. The method of claim 1, wherein said normalized intrinsic spectrum is obtained by normalizing an Integrated Intrinsic Absorption Profile and an Integrated Intrinsic Emission Profile of the sample material.

7. The method of claim 6, wherein said normalized Integrated Intrinsic Absorption Profile and said normalized Integrated Intrinsic Emission Profile are obtained by the following equations, respectively:

$$\text{Normalized } IIAP = IIAP \times NF_{norm}$$

$$\text{Normalized } IIEP = IIEP \times NF_{norm};$$

where IIAP is the Integrated Intrinsic Absorption Profile of the sample material, IIEP is the Integrated Intrinsic Emission Profile of the sample material and $NF_{norm}$ is a normalized noise factor.

8. The method of claim 1, wherein said plurality of spectroscopic instruments comprises spectral cameras covering different wavelength ranges associated to data on a pixel of a spatial field of view of a spectral data cube.

9. The method of claim 8, wherein each pixel comprises intrinsic spectral data of the spatial field of view for a wavelength range covered by all the plurality of spectral cameras.

10. The method of claim 8, wherein the intrinsic spectra of the sample material is obtained from said data cube comprising a plurality of pixels containing data of said spatial field of view.

* * * * *